(12) United States Patent
Hoeg et al.

(10) Patent No.: US 7,374,533 B2
(45) Date of Patent: May 20, 2008

(54) TIP STRUCTURE FOR VARIABLE DIRECTION OF VIEW ENDOSCOPE

(75) Inventors: Hans David Hoeg, Arcadia, CA (US); Nathan Jon Schara, Pasadena, CA (US); Eric Lawrence Hale, Altadena, CA (US)

(73) Assignee: Karl Storz Development Corp., Goleta, CA (US)

( * ) Notice: Subject to any disclaimer, the term of this patent is extended or adjusted under 35 U.S.C. 154(b) by 451 days.

(21) Appl. No.: 11/054,068

(22) Filed: Feb. 9, 2005

(65) Prior Publication Data

US 2005/0215860 A1   Sep. 29, 2005

Related U.S. Application Data

(60) Provisional application No. 60/556,603, filed on Mar. 26, 2004.

(51) Int. Cl.
*A61B 1/00* (2006.01)

(52) U.S. Cl. .................. 600/173; 600/128; 600/129

(58) Field of Classification Search .............. 600/128, 600/129, 30, 173
See application file for complete search history.

(56) References Cited

U.S. PATENT DOCUMENTS

| | | | |
|---|---|---|---|
| 3,856,000 A | 12/1974 | Chikama | 128/6 |
| 3,896,793 A * | 7/1975 | Mitsui et al. | 600/104 |
| 4,697,577 A | 10/1987 | Forkner | 128/6 |
| 5,313,306 A | 5/1994 | Kuban et al. | 348/65 |
| 5,653,677 A * | 8/1997 | Okada et al. | 600/112 |
| 5,762,603 A | 6/1998 | Thompson | 600/112 |
| 5,800,341 A | 9/1998 | McKenna et al. | 600/109 |
| 5,935,057 A * | 8/1999 | Lichtman et al. | 600/137 |
| 6,371,909 B1 | 4/2002 | Hoeg et al. | 600/173 |
| 6,500,115 B2 | 12/2002 | Krattiger et al. | 600/173 |
| 6,560,013 B1 | 5/2003 | Ramsbottom | 359/431 |
| 6,648,817 B2 | 11/2003 | Schara et al. | 600/173 |
| 2002/0049367 A1* | 4/2002 | Irion et al. | 600/173 |
| 2003/0032863 A1* | 2/2003 | Kazakevich | 600/173 |
| 2007/0032700 A1* | 2/2007 | Fowler et al. | 600/173 |

* cited by examiner

*Primary Examiner*—John P. Leubecker
(74) *Attorney, Agent, or Firm*—St. Onge Steward Johnston & Reens LLC (57) ABSTRACT

A variable direction of view endoscope generally comprising an endoscope shaft, an objective optical system disposed in the distal end of the shaft that defines a view vector movable relative to the longitudinal axis of the shaft, and a viewing window located in the distal end of the shaft through which the view vector scans over a range of different view vector directions when moved relative to the longitudinal axis of the shaft. A portion of the distal section of the endoscope shaft adjacent and proximal to the viewing window has a cross-section perpendicular to the longitudinal axis of the shaft, and at least two regions within the cross section are connectable by a straight line that does not lie within or on the boundary of the cross section. In certain embodiments, cross section comprises at least two disjoint closed sets of points.

15 Claims, 7 Drawing Sheets

Prior Art

TIP STRUCTURE FOR VARIABLE DIRECTION OF VIEW ENDOSCOPE

CROSS-REFERENCE TO RELATED APPLICATIONS

This application claims the benefit of U.S. provisional application Ser. No. 60/556,603 filed on Mar. 26, 2004, entitled "Tip structure for a variable direction of view endoscope", the contents of which are incorporated herein by reference.

FIELD OF THE INVENTION

The present invention relates to variable direction of view endoscopes.

BACKGROUND OF THE INVENTION

One of the shortcomings with rigid variable direction of view endoscopes, as disclosed in U.S. Pat. No. 3,856,000 to Chikama, U.S. Pat. No. 6,371,909 to Hoeg, U.S. Pat. No. 6,560,013 to Ramsbottom, U.S. Pat. No. 4,697,577 to Forkner, U.S. Pat. No. 6,500,115 to Krattiger et al., and U.S. Pat. No. 5,762,603 to Thompson, U.S. Pat. No. 5,313,306 to Kuban, and U.S. Pat. No. 5,800,341 to McKenna et al., is their limited retrospective viewing ability. Retrospective viewing would be important in industrial or medical diagnoses because mechanical cracks or tumors sometimes develop in locations which are posterior to the endoscopic insertion port. The main reason scopes have limited retrospective viewing ability is that the endoscope shaft itself blocks an angular region around the shaft. Having the optical objective system protrude beyond the outer diameter of the shaft is not desirable because generally endoscopes must be able to slide easily in and out of guide tubes or natural lumens, and designs with retractable objective systems, as disclosed in U.S. Pat. No. 6,371,909 to Hoeg et al., are not practical. U.S. Pat. No. 6,648,817 to Schara et al. teaches a tip construction which has a swept back region of reduced cross sectional area directly behind the viewing window to allow for extreme retrospective viewing. It is designed such that the viewing window is contained within the circumference of the endoscope shaft in order to minimize the chance of the viewing window getting snagged or bumped during insertion, retraction, and use of the endoscope, but the viewing window is still relatively exposed and unshielded. Even though scope viewing windows are made of tough scratch resistant materials (sapphire), exposure is a problem, particularly in harsh applications such as inspection of industrial machines or arthroscopic surgery where the scope typically is accompanied by steel tools rotating at high rpm. Traditional fixed angle endoscopes do not have this problem because they only need the viewing window to cover a small angle and can therefore be recessed into the surrounding tip structure for maximal protection.

Accordingly, the object of the present invention is to provide variable direction of view endoscopes with a tip structure which shields the viewing window but still allows retrospective viewing. Another object of the present invention is to provide a tip structure which is less prone to getting snagged. Still further objects and advantages such as simplified construction, assembly, and alignment will become apparent from the ensuing description and drawings.

BRIEF SUMMARY OF THE INVENTION

In accordance with the present invention, a variable direction of view endoscope has a robust tip that allows wide range viewing and prevents snagging.

DETAILED DESCRIPTION OF THE INVENTION

The following detailed description illustrates the invention by way of example, not by way of limitation of the principles of the invention. This description will enable one skilled in the art to make and use the invention, and describes several embodiments, adaptations, variations, alternatives and uses of the invention, including what we presently believe is the best mode of carrying out the invention.

Prior Art Devices

Figure 1A:
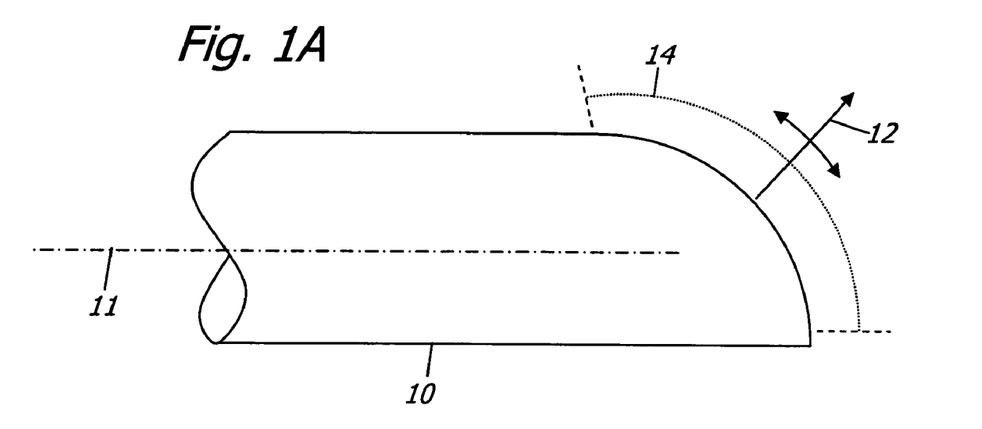
FIGS. 1A and 1B show retroviewing endoscopes according to the prior art.
Figure 1B:
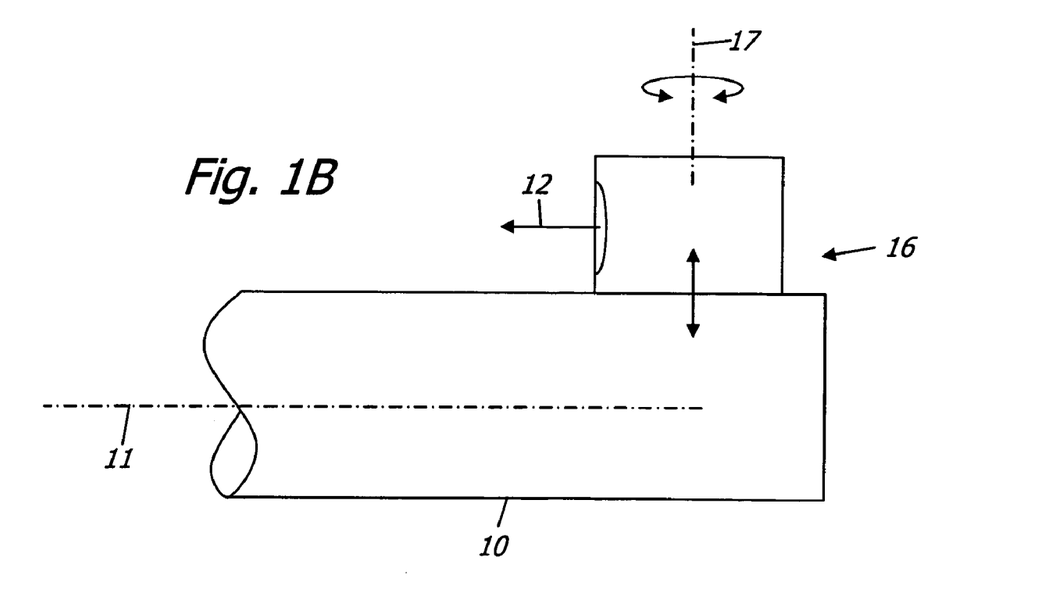

Referring now to the drawings, in which like reference numbers represent similar or identical structures throughout, FIG. 1 is a diagram of the distal section of an endoscope 10 with a longitudinal axis 11 and a variable view vector 12 which can swing through a range 14. With this type of design, the range 14 can be up to about 135 degrees measured from the forward viewing configuration. The retrospective angle is limited by the fact that shaft of the endoscope 10 blocks the line of sight once the angle gets large enough. FIG. 1B shows a design with a retractable viewing mechanism 16 intended to increase the retrospective viewing capability of the endoscope 10. While this mechanism, rotatable about an axis 17 transverse to the longitudinal axis 11, is capable of looking directly backwards, it is not practical because of its complexity and it also has significant sealing problems.

Figure 2A:
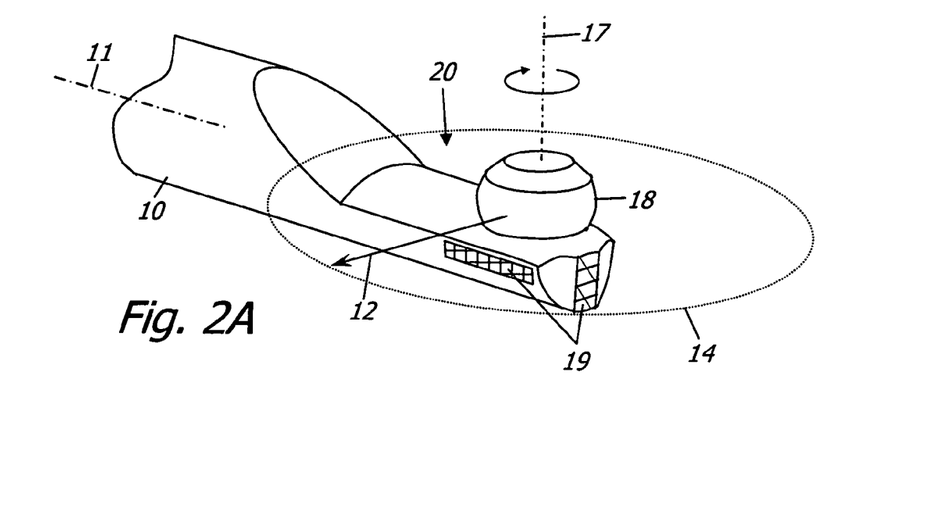
FIGS. 2A and 2B show another retroviewing endoscope according to the prior art.
Figure 2B:
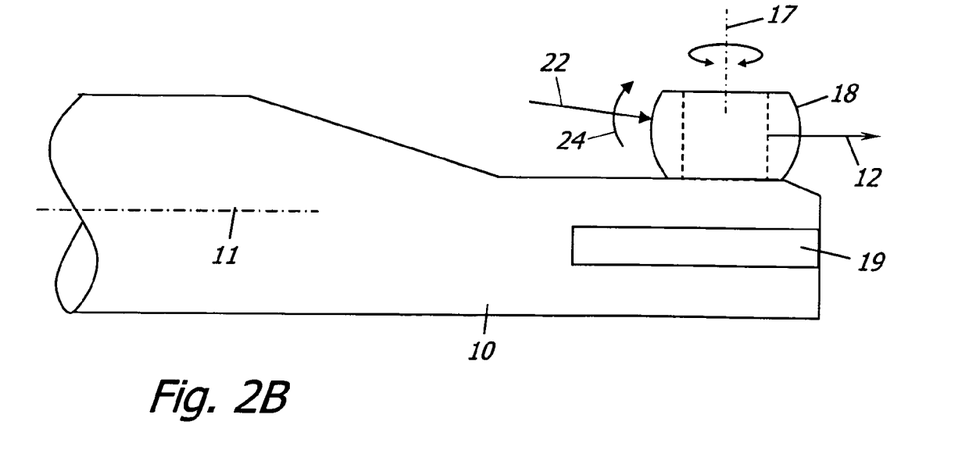
Figure 2C:
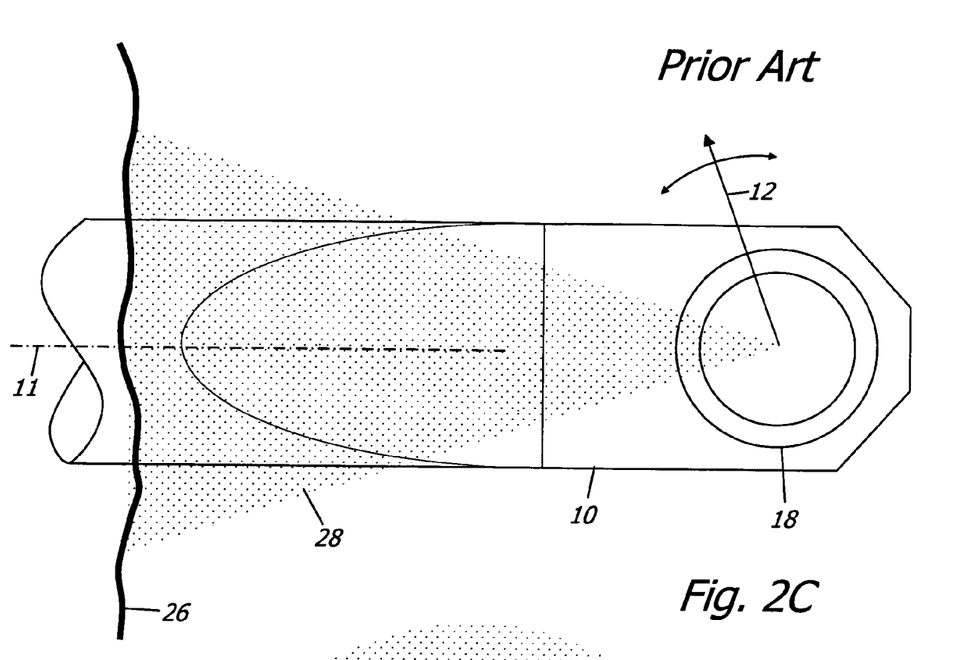
FIG. 2C shows a top view of the endoscope of FIGS. 2A-B and its angular blind zone.
Figure 2D:
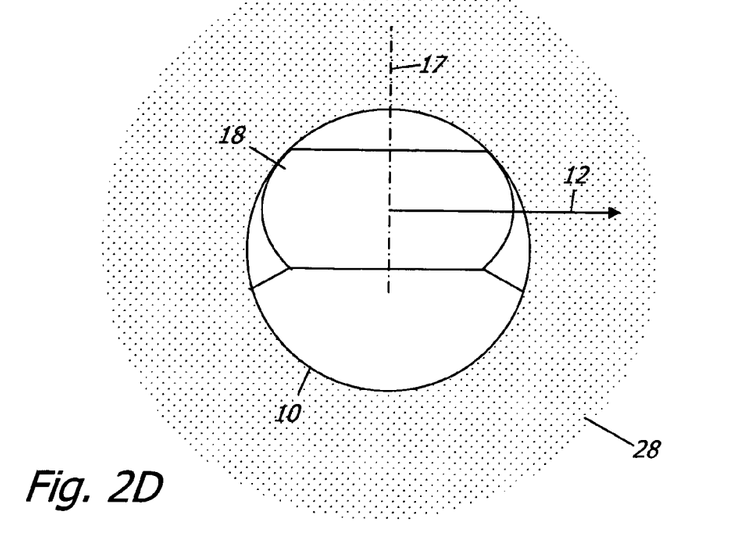
FIG. 2D shows a front view of the endoscope of FIGS. 2A-B and its angular blind zone.

FIG. 2A illustrates a tip design which avoids a retractable viewing mechanism and still provides extreme retrospective viewing. A viewing window 18 (and illumination windows 19) is seated in a recessed portion 20 of the tip and allows the view vector 12 to scan through an unlimited range 14. The recessed portion 20 has a smaller cross sectional area than the rest of the endoscope shaft 10, thus reducing the visual obstruction behind the viewing window 18 and opening up the retrospective viewing angle. A weakness with this design is that the viewing window 18 is not shielded and is therefore more readily damaged. Another problem, shown in FIG. 2B, is that environmental forces 22 cause moments 24 which tend to pry the viewing window 18 lose from the tip structure 10. Finally, the recessed portion 20 allows for the endoscope 10 to snag as it is retracted, even though the viewing window 18 fits completely within the circumference of the endoscope shaft 10. FIGS. 2C and 2D show top and front views of this design when inserted through a parietal wall 26 and its inherent angular blind zone 28.

Preferred Embodiment

Figure 3A:
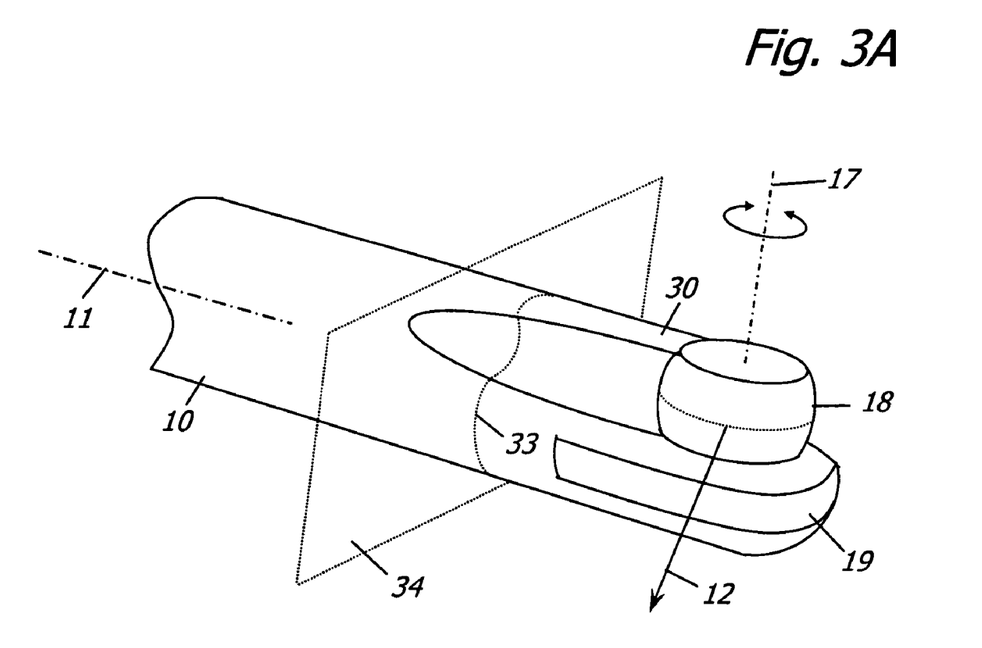
FIGS. 3A and 3B show an embodiment of the present invention using a ridge to protect and support the endoscope viewing window.
Figure 3B:
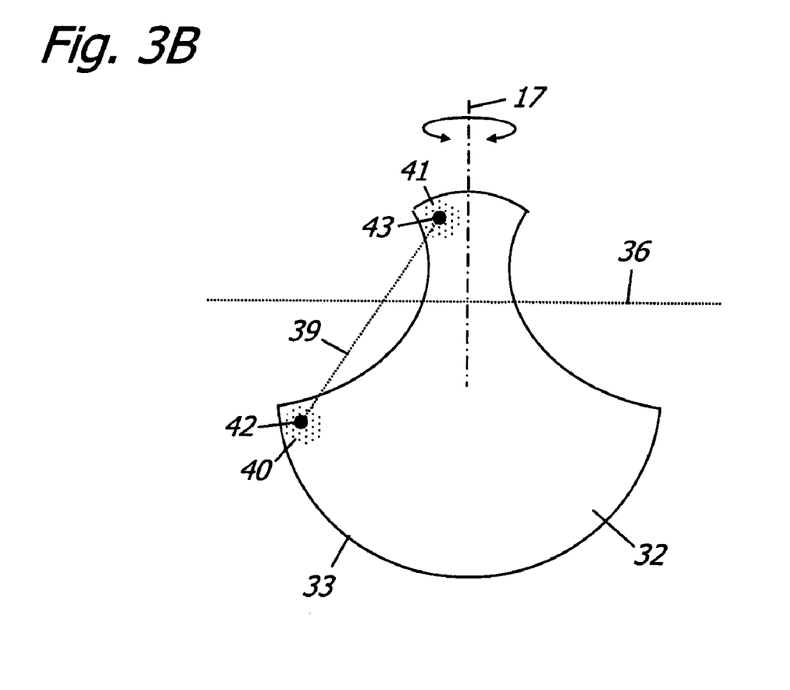

In the embodiment shown in FIG. 3A, the recessed section of FIG. 2A includes a ridge 30 which extends forward to the viewing window 18. There are three specific advantages with this tip design over the prior art: i) the ridge 30 prevents the viewing window 18 from getting snagged because it deflects environmental forces from the back which would otherwise stress and torque the viewing window 18; ii) the ridge 30 provides additional support for the viewing window 18 to withstand frontal and lateral forces; and iii) it still allows extreme retrospective viewing. A cross section 32 of this design, delimited by a boundary 33, and generated by a slice plane 34, is shown in FIG. 3B, along with the view vector scan plane 36 and the view vector pivot axis 17. The cross section 32 is defined to be the closed connected set of all points contained within and on the boundary 33. A region of this section 32 is defined as the neighborhood of points within the section 32 surrounding any point within the section 32. A straight line 39 can be used to connect two regions 40, 41 surrounding two points 42, 43 of the section 32 without the line 39 itself being contained within the section 32.

Figure 4A:
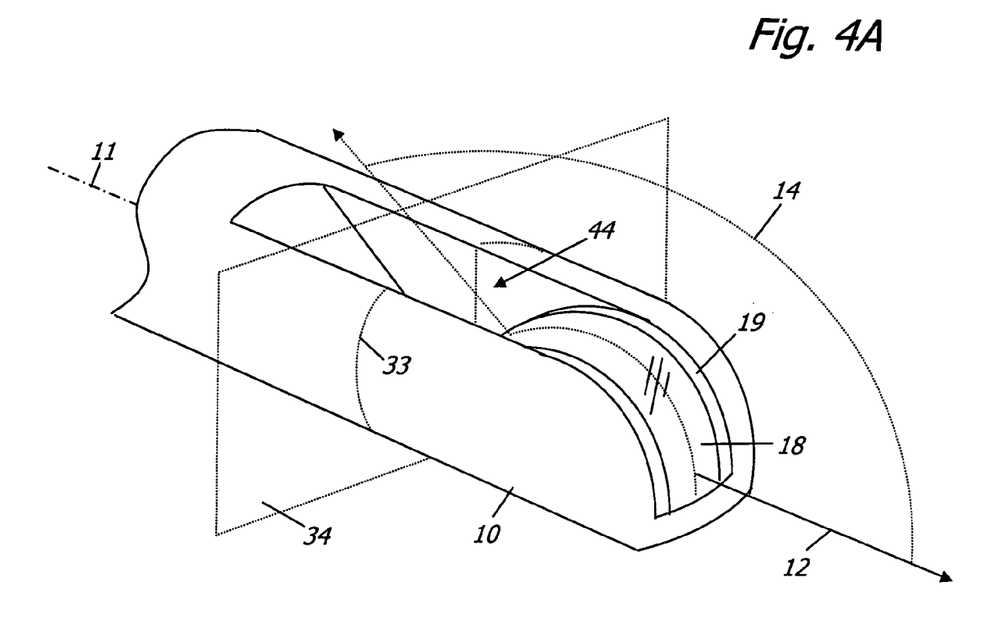
FIGS. 4A and 4B show an embodiment of the present invention using a slot to protect and support the viewing window but also allow an extreme retrospective viewing angle.
Figure 4B:
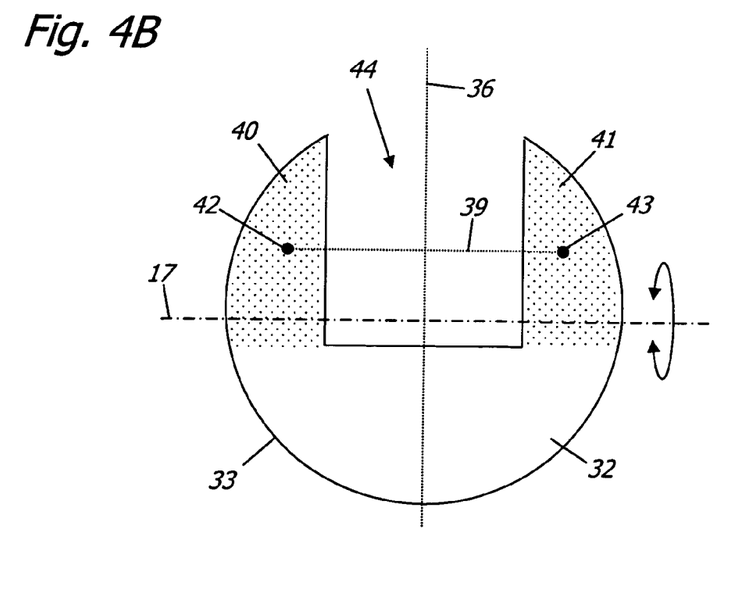

FIG. 4A shows an even more robust embodiment of a tip for a variable direction of view endoscope. In this embodiment the viewing window 18 is not axisymmetric—the endoscope shaft 10 must be rotated about its longitudinal axis 11 to achieve maximum viewing coverage—and is housed in a slot 44 which provides support on both sides. Because the window 18 is recessed into the slot 44, it is well protected from environmental forces and does not cause snagging. The slice plane 34 generates the cross section 32 show in FIG. 4B, and a straight line 39 can be used to connect the two regions 40, 41 surrounding the two points 42, 43 of the section 32 without the line 39 itself being contained within the section 32.

Figure 5A:
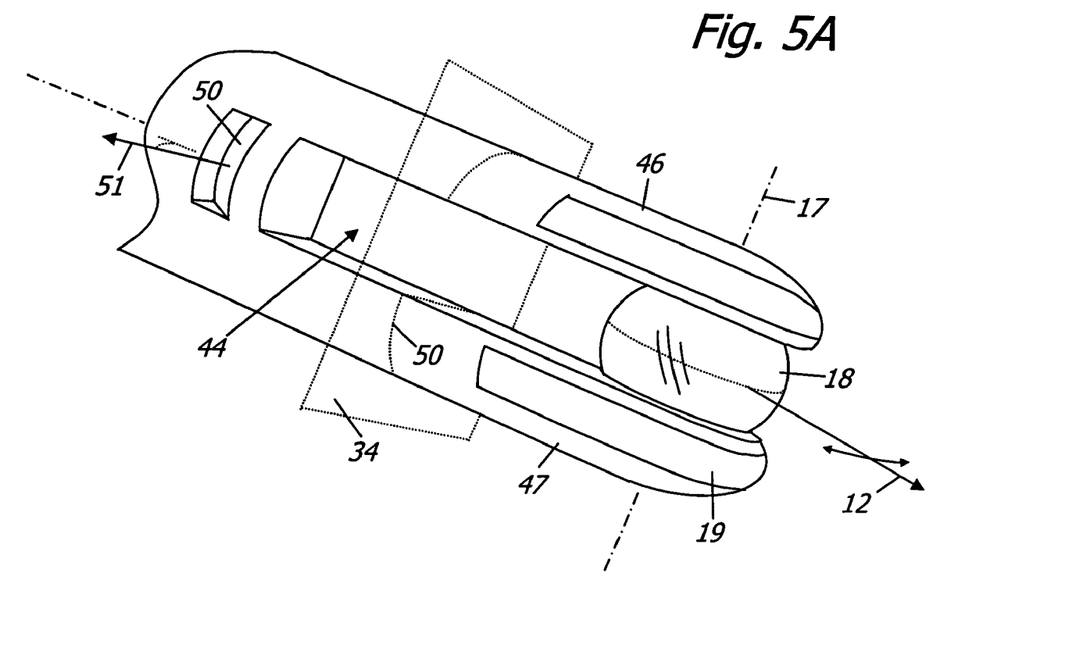
FIGS. 5A, 5B, 5C, and 5D embodiments of the present invention using a dual-prong approach to maximize the endoscopic viewing range and protect the viewing window.
Figure 5B:
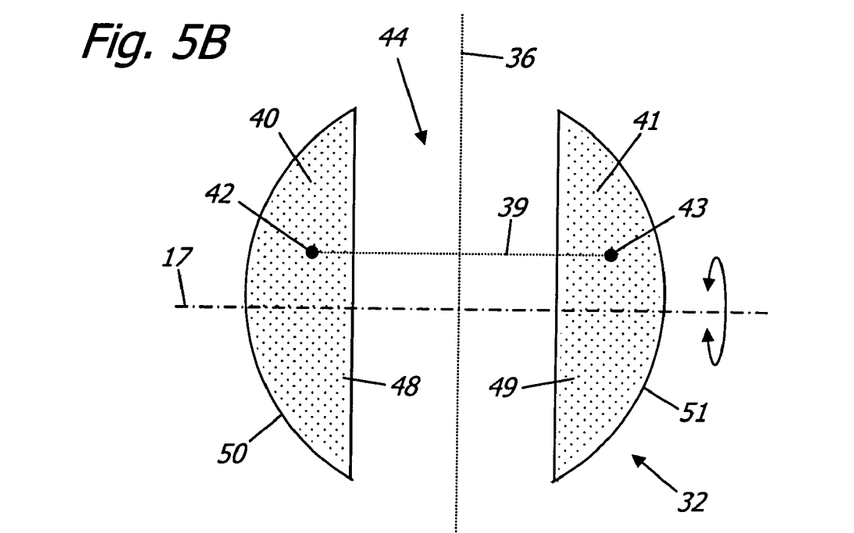
Figure 5C:
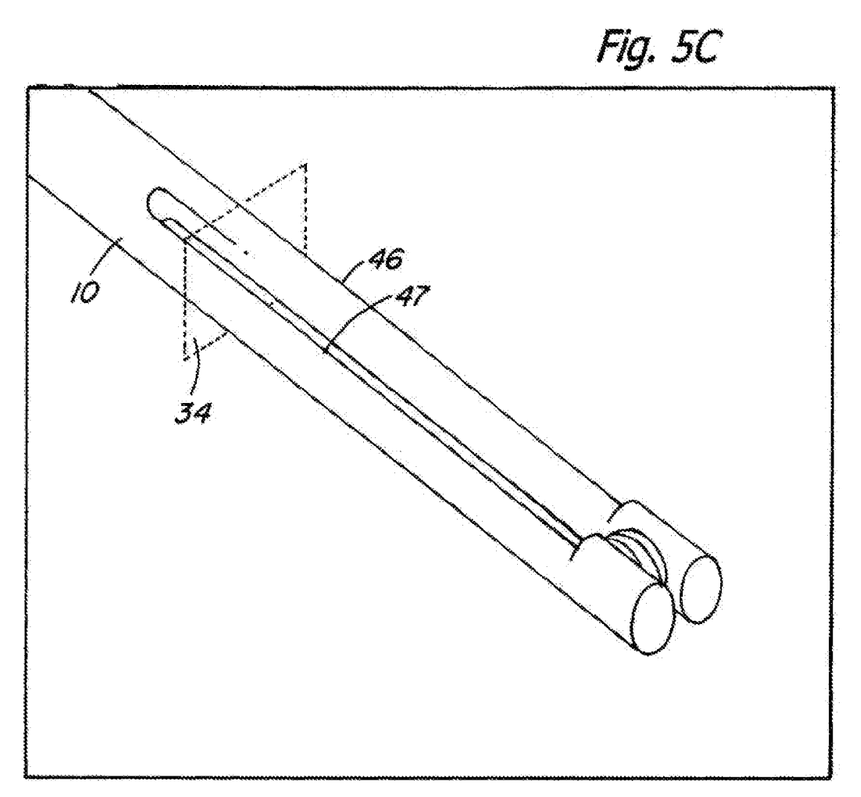
Figure 5D:
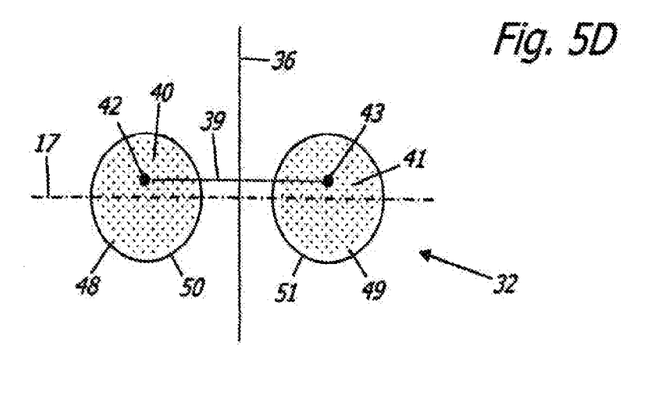

FIG. 5A shows a slightly less robust embodiment than that of 4A, but it affords increased retrospective viewing capability and also an unlimited range 14 about the pivot axis 38. The slot 44 of FIG. 4A has in this case been extended transversely through to the scope shaft 10, sandwiching the viewing window 18 between two prongs 46, 47 and opening up the entire space behind the viewing window 18. The slice plane 34 generates the cross section 32 shown in FIG. 5B. Note that the section 32 in this case consists of two disjoint closed sets of points 48, 49 with boundaries 50, 51. A straight line 39 can be used to connect the two regions 40, 41 surrounding the two points 42, 43 of the section 32 without the line 39 itself being contained within the section 32. FIGS. 5C and 5D show a variation of this dual-prong scheme.

The present invention has been described above in terms of a presently preferred embodiment so that an understanding of the present invention can be conveyed. However, many alternative designs and structural arrangements are possible without departing from the principle of the invention. The scope of the present invention should therefore not be limited by the embodiments illustrated, but rather it should be understood that the present invention has wide applicability with respect to multi-directional viewing instruments. All modifications, variations, or equivalent elements and implementations that are within the scope of the appended claims should therefore be considered within the scope of the invention.

We claim:

1. A variable direction of view endoscope, comprising:
   an endoscope shaft having a proximal section, a distance section, an interior defined by an outer wall, and a longitudinal axis; and
   a viewing window located in the distal section of said endoscope shaft through which the view vector defined by an objective optical system in the distal section scans over a range of different view vector directions when moved relative to the longitudinal axis of said endoscope shaft;
   wherein a portion of the distal section of said endoscope shaft adjacent and proximal to said viewing window has a cross-section perpendicular to the longitudinal axis of said endoscope shaft, wherein at least two regions within said cross section are connectable by a straight line that does not lie within or on the boundary of said cross section and does not lie within the interior of the shaft.

2. The endoscope of claim 1, wherein said cross section comprises at least two disjoint closed sets of points.

3. The endoscope of claim 1, wherein the view vector has a pivot axis angularly offset from the longitudinal axis of said endoscope shaft.

4. The endoscope of claim 3, wherein said pivot axis is substantially perpendicular to the longitudinal axis of the said endoscope shaft.

5. The endoscope of claim 1, wherein said viewing window fits completely within the circumference of said endoscope shaft.

6. The endoscope of claim 1, wherein:
   the distal section of said endoscope shaft has a slot defined by a base section and two side sections of said shaft; and
   said viewing window is disposed in said slot.

7. The endoscope of claim 1, wherein:
   the distal section of said endoscope comprises two prongs; and
   said viewing window is disposed between said prongs.

8. A method of obtaining a variable direction of view with an endoscope, comprising:
   providing an endoscope shaft having a proximal section, a distal section, an interior defined by an outer wall, and a longitudinal axis;
   pivoting a view vector through a viewing window located in the distal section of said endoscope shaft to scan over a range of different view vector directions;
   wherein a portion of the distal section of the endoscope shaft adjacent and proximal to the viewing window has a cross-section perpendicular to the longitudinal axis of the endoscope shaft, wherein at least two regions within the cross section are connectable by a straight line that does not lie within or on the boundary of the cross section and does not lie within the interior of the shaft.

9. The method of claim 8, wherein said cross section comprises at least two disjoint closed sets of points.

10. The method of claim 8, wherein the view vector is defined by an objective optical system in the distal section of the endoscope shaft.

11. The method of claim 8, wherein the view vector has a pivot axis angularly offset from the longitudinal axis of said endoscope shaft.

12. The method of claim 11, wherein said pivot axis is substantially perpendicular to the longitudinal axis of the said endoscope shaft.

13. The method of claim 8, wherein said viewing window fits completely within the circumference said endoscope shaft.

14. The method of claim 8, wherein:
the distal section of said endoscope shaft has a slot defined by a base section and two side sections of said shaft; and
said viewing window is disposed in said slot.

15. The method of claim 8, wherein:
the distal section of said endoscope comprises two prongs; and
said viewing window is disposed between said prongs.

* * * * *